United States Patent [19]

Gazzani

[11] Patent Number: 4,808,415

[45] Date of Patent: Feb. 28, 1989

[54] COMPOSITION FOR THE EXTEMPORARY PREPARATION OF FORMULATIONS FOR TOPICAL APPLICATIONS FOR PHARMACEUTICAL AND COSMETIC USE

[75] Inventor: Giovanni Gazzani, Appiano Gentile, Italy

[73] Assignee: Crinos Industria Farmacobiologica Spa, Como, Italy

[21] Appl. No.: 195,582

[22] Filed: May 16, 1988

Related U.S. Application Data

[63] Continuation of Ser. No. 9,436, Feb. 2, 1987, abandoned.

[30] Foreign Application Priority Data

Feb. 4, 1986 [IT] Italy .............................. 19284 A/86

[51] Int. Cl.⁴ .......................... A61K 7/00; A61K 7/32

[52] U.S. Cl. .................................................. 424/488

[58] Field of Search .................. 424/488, DIG. 5, 69, 424/324

[56] References Cited

U.S. PATENT DOCUMENTS 4,097,606  6/1978  Chavkin et al. ...................... 424/324

Primary Examiner—Nancy A. B. Swisher
Attorney, Agent, or Firm—Armstrong, Nikaido, Marmelstein & Kubovcik

[57] ABSTRACT

A composition for the extemporary preparation of gels and creams for topical application and for pharmaceutical and cosmetic use comprises, besides one or more ingredients active under the pharmacological and/or cosmetic point of view, a gum swellable in water and a permeation agent.

12 Claims, No Drawings

COMPOSITION FOR THE EXTEMPORARY PREPARATION OF FORMULATIONS FOR TOPICAL APPLICATIONS FOR PHARMACEUTICAL AND COSMETIC USE

This is a continuation application of Ser. No. 009,436, filed Feb. 2, 1987 now abandoned.

The present invention relates to a composition for the extemporary preparation of formulations for topical application, particularly gels and creams, for pharmaceutical and cosmetic use.

The most widespread pharmaceutical and cosmetic forms for topical cutaneous application comprise:

CREAMS OR MILKS

These are emulsion of oil in water or water in oil containing emulsifiers of several types, fats, oils, waxes and water in different proportions.

OINTMENTS AND FATTY STICKS

They consist prevailingly of oils, waxes and fats with or without emulsifiers, characterized by a very reduced content or by the total absence of water.

GELS

These are usually transparent forms, the consistency of which varies from the gelatinous to a very fluid state, prevailingly consisting of vegetal polysaccharides such as arabic gum, tragacanth gum, carrageenin, alginic acids, etc, or synthetic polymers such as carboxyvinyl polymer (carbopol) variously salified and cellulose derivatives.

All these polymers form gels with water, the consistency of which is proportional to the concentration and which are variously spreadable, acceptable for the skin and of pleasant feeling.

LOTIONS

These usually consist of a fluid solvent (water or water-alcohol mixtures, water-glycerin mixtures, etc.) which, owing to their fluidity, are generally applied onto the skin by means of a napkin or cotton flock.

ASPERSING POWDERS, TALCS AND POWDERS

These are based on talc, kaolin, silica, lactose, mannitol, waxes and micronized fats, etc. which upon being applied onto the skin form a thin film of protecting powder.

All these vary common pharmaceutical and cosmetic forms show, alternatively, some drawbacks, which in some cases render their use difficult or even practically not possible.

The emulsions of oil in water and of water in oil (creams and milks) are bases unsuitable as vehicles for substances not stable in the presence of water, such as antibiotics, enzymes or anyhow active principles readily degradable in solution. They are moreover of difficult storage and physically poorly stable. The presence of emulsifiers sometimes makes it not certain the skin compatibility, mainly for continuous and extended uses. It is also worth to note that in the emulsions the development of bacteria and mycetes takes readily place and the preservants which can be used are not always sufficient in order to inhibit any microbial growth. The use of ointments (without water) might partially solve these problems, but these fatty bases are of unpleasant application, and cause the garments to be smeared and soiled; moreover the fatty layer applied to the skin may constitute a barrier, both for the normal skin transpiration and for the absorption of the active principles, the latter being included in a vehicle of difficult permeation.

Gels and lotions comprising water are affected by the same problems of stability of the substances degradable into contact with water and although exhibiting, mainly as regards gels, undeniable advantages over the emulsions from the point of view of both the physical stability and of ready and pleasant use, still show problems of degradation induced by microorganisms, even if in a reduced degree.

The aspersing powders, which do not contain water, are undoubtedly the most adequate vehicle for the active compounds raising problems of chemical stability and also possess the undeniable advantage of not permitting, during the storage, any microbial growth.

However their application is precarious and hardly quantitatively determinable; moreover it is easily foreseeable that the active substances, dispersed in solid state in the powder, shall not come into intimate contact with the skin and thus their activity is not exploited in a complete, exhaustive and above all constant manner as it occurs when the presence of a solvent leads not only to a more intimate contact with the skin but also to a better surface dispersion.

As it can be noticed, none of the usual preparations for topical use is fully free from drawbacks, whereby it is necessary from time to time to choice that formulation seemingly most convenient for the requirements of stability, storage, functionality and practicalness related to the nature of the substances being used and, obviously, to the end purpose of the formulation.

In order to obviate to the above mentioned drawbacks it would be necessary to be able to prepare extemporary pre-dosed creams or gels in which the solvent (water) can be added a few instants before the use on the skin or the mucosae.

The attempts to date made for the preparation of these extemporaneously formulations for topical use did not lead to practical results since the time needed for the absorption of the solvent were very great so that the product was practically useless for the inteded use. Furthermore the gums usually used form with water unpleasant lumps the dissolution of which is very difficult.

In the DE-PS 862,044 a process is described for the manufacturing of powder formulations to be used for the extemporary preparation of a base for ointments or directly of the ointment.

The composition of said powder is as follows:

carboxymethylcellulose 30–45% clay swellable in water (bentonite, Fuller's earth, etc.) 30–45% wetting agent (aliphatic or aromatic sulfonic acids) 3–6% buffer agent, to adjust pH in the range 6–6.5, from 0.4 to 0.8% bacteriostatic agent 3–7% diluent (preferably lactose or similar carbohydrates) 8% at maximun active compound 1–25%.

In the examples of the preparation of the extemporary cream the stirring of the initial water suspension is carried out to promote the dissolution. Said operation may have a duration of 30 minutes (ex. 1) or of 0.5 to 1 minute (ex. 2).

In turn French Pat. No. 2.311.530 discloses a powder or granule composition for the extemporary preparation of ointments.

The composition is characterized in that it contains a carboxyvinylpolymer, having molecular weight of between 860,000 and 1,000,000, insoluble but swellable in water, in a concentration of 1 to 10% by weight.

The other components for the formulation are the following:

alkalinizing agents (e.g. ammonium or potassium carbonate) 2-5% emulsifier of the type oil in water (e.g. sodium stearate, sodium dioctylsulfosuccinate, etc., preferably sodium laurylsulfate) 0.5-2% fatty substances (e.g. liquid paraffin, triglycerides, decyl ester of oleic acid, cetyl alcohol, isopropyl miristate) 1-30%.

To the said composition other thickening agents can be added such as starch, celluloses, colloidal silica, etc. in an amount of 10 to 90%. The ointment is readily prepared by admixing one part of granules or powder having the above composition with 8 parts of water and mixing for a time of 1 to 2 minutes.

The French Pat. No. 2,068,447 relates to compositions permitting an aqueous preparation for dermatological or cosmetic use to be obtained as well as to their preparation method.

Said compositions are in form of a lyophilizate directly obtained from an emulsion of the oil in water type essentially containing:

one or more active principles for dermatological or cosmetic use;

a lipidic phase containing fatty acids and their derivatives, fatty alcohols and their derivatives, natural and synthetic fats;

a hydrophilic phase consisting of a thickening agent and of an emulsifier in water. As thickeners natural gums, cellulose derivatives, pectines, bentonite and colloidal silica, polysaccharides, synthetic macromolecules and starches can be used. As emulsifiers use can be made of anionic, cationic, non ionic surface active compounds, or salts of organic acids or fatty alcohols oxyethylene derivatives.

In the specification of this patent it is stated that the granules as such must not be put directly into contact with the water, since they tend to soften thus hindering the dissolution process.

In order to eliminate this drawback these granules are wrapped up in a bag of wide weft cloth, so as to permit the free passage of the water as well as of the emulsion, once it is reconstituted.

Said bags are in turn enclosed in paper or aluminum bags, possibly combined with plastic material.

In the French Pat. No. 2,101,044 a like composition is disclosed but particularly directed to shampooing, hair lotion and tooth paste formulations.

A modification is described of the preparation of the dry residue to be later dissolved in water to reconstitute the emulsion. In this case the solution, before the lyophilization, is absorbed in a poliurethane foam "sponge".

In this case the emulsion reconstitution takes place by simple immersion of the sponge in water; however the residue part contained in the innermost part of the sponge shall start to dissolve only when that of the outermost parts of the sponge are already dissolved.

U.S. Pat. No. 2,484,637 relates to a base for the extemporary preparation of ointments, in form of an anhydrous powder comprising methylcellulose and sorbitol in the proportion of 10 to 40 parts of sorbitol for 100 parts of methylcellulose.

The powder dissolution in water takes about one minute.

Such a preparation does not swell, since methylcellulose is a water soluble polymer.

It has now been surprisingly found and is the subject of the present invention that compositions comprising a gum capable of fixing water or swellable in water, i.e. carboxymethylstarch, provided that it is combined with a cellulose as a permeating agent, when put into contact with water form almost istantaneously gels and creams of easy and ready applicability to the skin.

It has been furthermore found that the compositions according to the present invention can be suitably dosed in form of tablets having a predetermined water absorption and thus an adjustable viscosity or consistency.

Of course the compositions according to the present invention contain one or more active compounds having the desired topic effect.

As regards the carboxymethylstarch, the content thereof in the composition of the invention may range from 10 to 50% by weight, whereas as regards the celluloses, as permeating substance, their content in the composition of the invention is of between 1 and 50% by weight.

The function of the cellulose is that of absorbing the solvent (water) without being dissolved and permit it to reach in every part of the tablet the gum which is thus almost istantaneously swelled.

From the field experiments it was found that:

(a) the tablet according to the invention is swelled in water in a maximum time of one minute forming a soft, voluminous gel, which can be easily topically applied;

(b) the amount of absorbed water varies from 5 to 10 times the weight of the tablet and gives place to an increase, in about the same ratio, of the gel volume with respect to the initial one of the tablet, (c) the addition of a hydrophilic but water insoluble polymer, i.e. the cellulose, permits the almost instantaneous absorption of the water, which otherwise, in the presence of only carboxymethylstarch, would take place much more slowly.

With the compositions according to the invention it is possible to prepare any pharmaceutical formulation for topical use and any cosmetic and more precisely:

gels with active compounds not stable in water solution (e.g. some antibiotics);

antiacne, hair detergent, after-shave, skin protecting, anti-cellulitis, anti-transpirant, deodorizing, hair-removing, nutrient and hydrating, skin detergent, intimate hygiene preparations.

Among the advantages of the present invention, apart from the stability and from the practicalness of use, the elimination of water is to be mentioned, the latter being usually the prevailing part of the product sold to the customers.

Some examples of compositions and formulations according to the invention are given hereinafter, clearly of having exemplifying but non limiting purpose.

EXAMPLE 1

Tablets for an anti-acne extemporary gel 25 g of carboxymethylstarch, 50 of zinc oxide, 5 g of colloidal sulfur, 50 g of microgranular cellulose and 0.05 g of Triclosan are precisely weighted and then sieved through a 40 mesh sieve; thereafter the powders are admixed in a laboratory mill for 15 minutes.

The said mixture is then charged in the tank of a manual press having a 7.5 mm punch. There are obtained about 500 tablets, each of the weight of 270 mg, with a hardness of between 3 and 4 kg.

On a watch glass placed onto a laboratory balance 8 tablets as above prepared are positioned in sequence.

On each tablet, by means of a pipette, water is added in form of a thin stream with a constant flow rate of 100 microliters/second. It is seen that the tables are fully swelled up in an average time of 24±3 seconds. The amount of water absorbed is about 8 to 9 times the initial weith of the tablet.

The corresponding volume of the gel thus obtained is of between 2.5 and 3 ml.

Upon the water feeding is continued, the water is no longer absorbed and collected onto the glass.

EXAMPLE 2

Tablets for extemporary gel containing penicillin

Carboxymethylstarch: 0.100 g
microgranular cellulose: 0.100 g
penicillin: 250,000 U.I.

EXAMPLE 3

Tablets for extemporary cream containing tetracyclin carboxymethylstarch: 0.150 g
microgranular cellulose: 0.200 g
polyoxyethylensorbitan monostearate: 0.010 g
cetylstearyl alcohol: 0.100 g
tetracyclin: 0.046 g

EXAMPLE 4

Tablets for extemporary vaginal gel with trichomonacidal activity carboxymethylstarch: 0.350 g
cellulose: 0.200 g
metronidazole: 0.500 g

EXAMPLE 5

Tablets for extemporary vaginal hormonal cream carboxymethylstarch: 0.100 g
microgranular cellulose: 0.200 g
polyoxyethylenated castor oil: 0.050 g
spermaceti: 0.100 g
conjugated estrogens: 0.002 g

EXAMPLE 6

Tablets for extemporary hair shampooing gel carboxymethylstarch: 0.150 g
sodium laurylsulfate: 0.100 g
acylglutamate: 0.050 g
microgranular cellulose: 0.200 g

EXAMPLE 7

Tables for extemporary after-shave gel carboxymethylstarch: 0.100 g
cellulose: 0.100 g
azulene: 0.001 g
allantoin: 0.010 g

EXAMPLE 8

Tablets for extemporary cream carboxymethylstarch: 0.100 g
microgranular cellulose: 0.070 g
saccharose monopalmitate: 0.050 g
hydrogenated coconut oil: 0.020 g
bees wax: 0.050 g

EXAMPLE 9

Tablets for extemporary nutrient and hydrating cream

Carboxymethylstarch: 0.050 g
microgranular cellulose: 0.200 g
bees wax: 0.050 g
lanolin: 0.050 g
carob oil: 0.070 g
sodium piroglutamate: 0.005 g

I claim:

1. A method of topically applying at least one active ingredient to a patient, said method comprising providing an at least essentially anhydrous composition comprising said at least one active ingredient, carboxymethylstarch and water insoluble cellulose, said carboxymethylstarch and said cellulose being in solid and dry form,
    adding water to said composition to swell the composition and form a topical gel, cream or lotion, and
    applying the gel, cream or lotion to the patient.

2. Method of claim 1, wherein said composition contains about 10 to 50% by weight of said carboxymethylstarch and about 1 to 50% by weight of said cellulose.

3. A method of claim 1, wherein said essentially anhydrous composition is in the form of at least one tablet having a predetermined water absorption.

4. Method of claim 1, wherein said active ingredient is a pharmacologically active substance.

5. Method of claim 1, wherein said active ingredient is a substance having cosmetic action.

6. A composition in the form of a topical gel, cream or lotion formed by the addition of water to an at least essentially anhydrous composition comprising at least one active ingredient, carboxymethylstarch and water insoluble cellulose, said carboxymethylstarch and said cellulose in the anhydrous composition being in solid and dry form.

7. Composition of claim 6, wherein said essentially anhydrous composition contains 10 to 50% by weight of carboxymethylstarch.

8. Composition of claim 6, wherein said essentially anhydrous composition contains about 1 to 50% by weight of cellulose.

9. Composition of claim 6, wherein said essentially anhydrous composition is in the form of at least one tablet having a predetermined water absorption.

10. Composition of claim 6, wherein said active ingredient is a pharmacologically active substance.

11. Composition of claim 6, wherein said active ingredient is a substance having cosmetic action.

12. Method of claim 1, wherein water is added to said composition in an amount of at least 5 times the weight of the composition.

* * * * *